United States Patent [19]

Aillon

[11] Patent Number: 4,798,588
[45] Date of Patent: * Jan. 17, 1989

[54] CENTRAL VENOUS PRESSURE CATHETER AND METHOD FOR USING

[76] Inventor: Rene Aillon, 86 Crofut St., Pittsfield, Mass. 01201

[*] Notice: The portion of the term of this patent subsequent to Jul. 22, 2003 has been disclaimed.

[21] Appl. No.: 31,258

[22] Filed: Mar. 27, 1987

Related U.S. Application Data

[63] Continuation-in-part of Ser. No. 855,927, Apr. 25, 1986, abandoned, which is a continuation-in-part of Ser. No. 677,519, Dec. 3, 1984, Pat. No. 4,601,706.

[51] Int. Cl.$^4$ .............................................. A61B 5/02
[52] U.S. Cl. ..................................... 604/122; 604/45; 128/673
[58] Field of Search ................... 604/45, 122, 96–103, 604/49, 54, 280, 53; 128/672, 673, 675, 748, 348.1, 344, 642

[56] References Cited

U.S. PATENT DOCUMENTS

| 1,879,249 | 9/1932 | Honsaker | 604/280 |
| 3,593,713 | 7/1971 | Bogoff | 604/280 |
| 3,971,385 | 7/1976 | Corbett | 604/96 |
| 3,991,768 | 11/1976 | Portney | 604/10 |
| 3,995,623 | 12/1976 | Blake et al. | 128/642 |
| 4,140,119 | 2/1979 | Pollack | 604/53 |
| 4,285,341 | 8/1981 | Pollack | 604/53 |
| 4,301,797 | 11/1981 | Pollack | 604/53 |
| 4,329,993 | 5/1982 | Lieber et al. | 128/691 |
| 4,354,502 | 10/1982 | Colley et al. | 604/122 |
| 4,384,470 | 5/1983 | Fiore | 128/672 |
| 4,508,103 | 4/1985 | Calisi | 128/673 |
| 4,573,966 | 3/1986 | Weikl et al. | 604/53 |
| 4,601,706 | 7/1986 | Aillon | 128/673 |
| 4,621,654 | 11/1986 | Holter | 604/10 |
| 4,627,832 | 12/1986 | Hooven et al. | 604/9 |

FOREIGN PATENT DOCUMENTS

| 2632280 | 1/1978 | Fed. Rep. of Germany | 604/102 |
| 2737855 | 3/1979 | Fed. Rep. of Germany | 604/102 |
| 0694197 | 10/1979 | U.S.S.R. | 128/344 |

OTHER PUBLICATIONS

Bulletin MP307, "CritiCath Heparin Coated Thermodilution Catheter Model SP5107"–by Gould Electronics & Electrical Products–2 pgs.
"Transseptal Left-Heart Swan-Ganz Catheterization", American Heart Journal, Mar. 1983, Kotoda et al., British Medical Journal, New Appliances, Feb. 25, 1967.
Surgical Forum #2, 1951, pp. 399–402, "Treatment of Hydrocephalus by Direct Shunt from Ventrical to Jugular Vein".

Primary Examiner—John D. Yasko
Attorney, Agent, or Firm—Arthur K. Hooks

[57] ABSTRACT

A central venous pressure catheter has a long flexible tube containing at least three channels or lumens. Toward the tip or distal end of the catheter are three ports in the wall of the tube each providing access to one of the lumens, respectively. An inflatable balloon, formed about the tube is located between a distal and a proximal of the ports and a balloon-inflating port lies within the balloon. The balloon is spaced away from the distal port by about 8 centimeters so that when the balloon is located in an upper region of the superior cava vein of an upright-positioned patient undergoing surgery of the head or neck, the balloon may be inflated just enough to raise the blood pressure at the site of the surgery to about equal that of the ambient atmosphere. There is thus no bleeding from cut veins and neither is there any tendency for cut veins to aspirate leading to an air induced embolism.

8 Claims, 2 Drawing Sheets

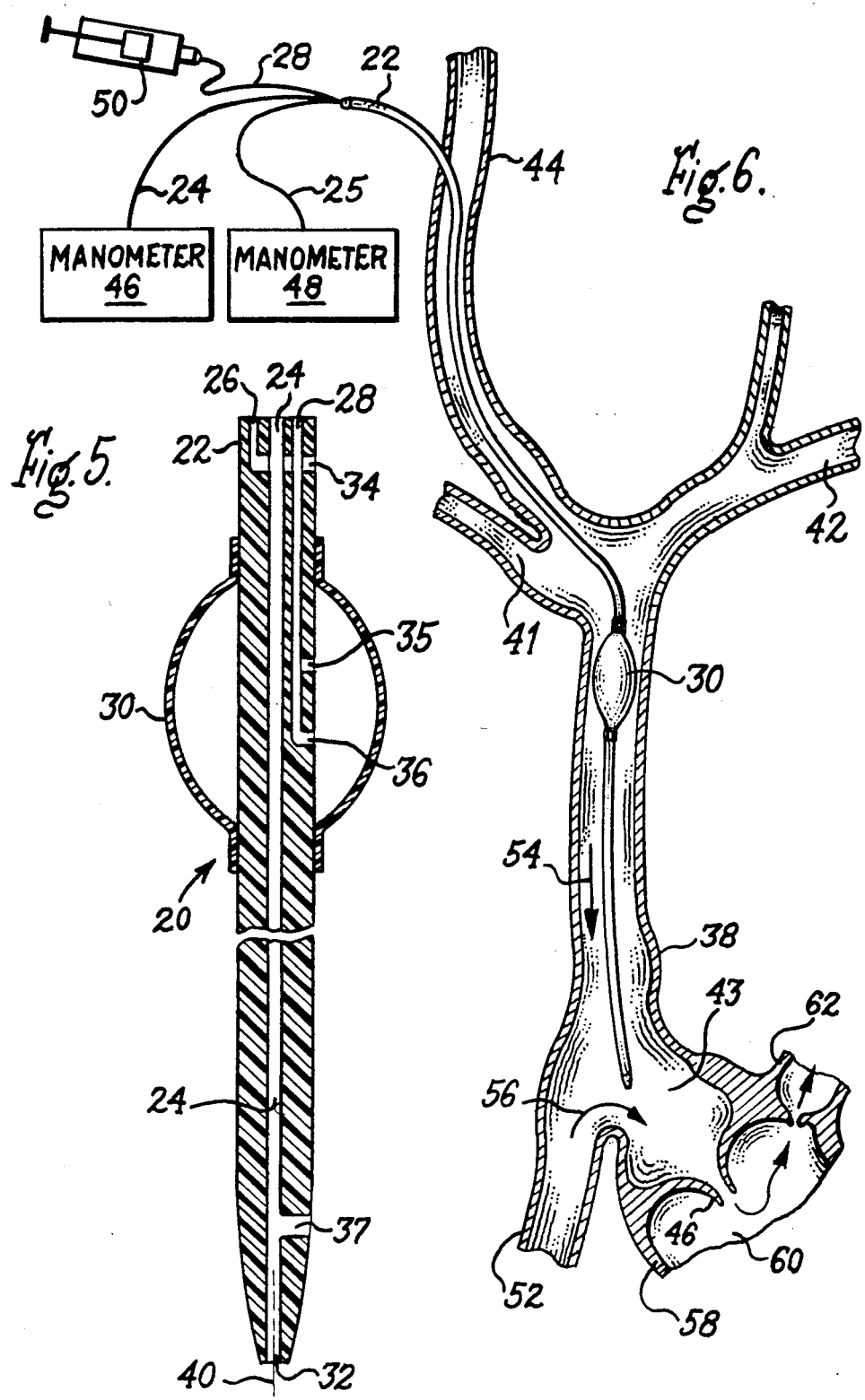

CENTRAL VENOUS PRESSURE CATHETER AND METHOD FOR USING

CROSS REFERENCE TO RELATED APPLICATION

This application is a continuation-in-part of my pending application Ser. No. 855,927 filed Apr. 25, 1986 now abandoned which is a continuation-in-part of the application Ser. No. 677,519 filed Dec. 3, 1984 that issued as U.S. Pat. No. 4,601,706 on July 22, 1986.

BACKGROUND OF THE INVENTION

This invention relates to a catheter for controllably obstructing the flow in a vein and more particularly to such a catheter having ports on either side of the obstruction for measuring the differential pressure therebetween as a measure of the degree of the obstruction obtained.

When surgery is performed on a patient in the supine (horizontal) position, which is done in the vast majority of cases, air embolism is not possible because pressure within the veins is greater than atmospheric pressure. For the supine patient, open veins bleed. However, when the patient is positioned in the sitting upright position, the pressure in the veins of the head and neck become negative in relation to atmospheric pressure, and those veins, if cut, readily draw in air. Air inside the circulatory system induces circulatory failure and poor pulmonary oxygenation, and a large embolus may induce the early demise of a patient.

Surgery in the upright position is a highly desirable condition sought by surgeons for certain types of operations including brain surgery, but the high probability of air aspiration into cut veins discourages and curtails this practice. Air embolism is a dreadful insidious condition which may totally overshadow gains obtained by performing surgery in the sitting position. Air embolism can successfully be detected, but treatment, while surgery is in progress can be a nightmare. Air embolism produces a frothy blood-air mixture which is difficult to aspirate and attempts at air removal are often fruitless, too late and lead to disastrous consequences.

It is therefore an object of this invention to provide a method for preventing air aspiration into cut veins and consequent air embolism during surgery of the head and neck of the patient in the sitting position, without adversely affecting the patient's normal physiology.

It is a further object of this invention to provide a catheter insertable into the patient's superior cava vein that includes a means for controllable partial obstruction of the superior cava vein and a means for measuring the differential venous blood pressure on either side of the blockage to guide blockage control.

SUMMARY OF THE INVENTION

This invention recognizes that the major lower portion of the superior cava vein is especially thin-walled and resilient; and further unlike most other veins it is not restrained from expanding either by connecting tissues or by encompassing body structure but instead "floats" freely in the thoracic cavity that houses the lungs. Thus, blood pressure within the superior cava vein tends, even when a person is in the upright position, to be at about ambient air pressure.

For related reasons, to be explained in the description below, the improved venous pressure catheter of this invention is comprised of a tube containing a plurality of lumens, a first of which lumens is accessible at the catheter tip end via a distal port and a second lumen is accessible through a proximal port in the side of the tube located about 10 centimeters from the distal port, and an inflatable balloon surrounds the tube and is located between the distal and proximal ports but closely adjacent to the proximal port.

The new venous-pressure control process that is made possible by the above-described catheter is as follows.

With the patient in a supine position, the catheter is inserted, distal tip first, into the jugular vein or into the subclavian vein and from there into a lower venous-system region including the right atrium (auricle) of the heart and about the lowest 2 centimeters of the superior cava vein. With the catheter in this location the patient is placed in an upright position and the balloon is inflated to produce a nearly zero hydrostatic pressure at the intended site of surgery of the head or neck. The pressure there is determined by measuring the differential pressure between the distal and proximal ports and accounting for the known distance between ports and the vertical distance between catheter tip and intended site of surgery. To adjust the pressure to slightly higher than zero would cause some slight bleeding from any cut veins there and will more reliably avoid negative venous pressures at the site of surgery that would lead to the dreaded air inspiration.

This process has several important advantages. First, the balloon is inflated at a higher region of the superior cava vein in which higher region the vein wall is less resilient with a relatively unchanging diameter than at points below. It has been discovered that inflated balloons at lower points in the cava vein cause the resilient vein walls to loosely distent about the balloon making the desired blood-flow valving action of the balloon difficult to control whereas this problem is greatly ameliorated by inflating the balloon within the higher region.

Secondly, the elongate tube region between the catheter tip and the balloon, permits another and simpler procedure relative to X-ray photography or fluoroscopy for accurate determination of the location of the catheter. That procedure entails initially inserting the catheter deep enough that the catheter tip passes through the mitral valve from the right atrium into the right ventricle of the heart. Evidence that this has been accomplished may be readily had by monitoring the pressure at the distal port which suddenly exhibits much more pronounced heart-pulse pressure excursions as soon as the mitral valve is penetrated. Next, the catheter is withdrawn about 2½ centimeters positioning the catheter tip and distal port at about the center of the above-noted lower 2 cm. of the superior cava vein and at the same time the balloon is positioned within the most narrow and least resilient uppermost portion of the superior cava vein.

Thirdly, the distal port is positioned within the reservoir (pre-load pressure region) of the blood that for a normal person in the upright position extends upward in the superior cava vein from the atrium 2 to 5 centimeters, and that serves to prime the heart pump. The blood pressure at the distal port is therefore approximately 2 to 5 centimeters $H_2O$ and is referred to herein as "pre-load pressure". Pressure measurements in the vertical superior cava vein are essentially zero, this being a blood-free-fall region, and a manometer measurement of this pressure will give misleading pressure indications.

BRIEF DESCRIPTION OF THE DRAWINGS

FIG. 5 shows in side sectional view an invasive-end portion of the catheter of this invention.

FIG. 6 shows in sectional view of an upper portion of the cardio-vascular system of an upright patient with the catheter of this invention properly inserted.

DESCRIPTION OF THE PREFERRED EMBODIMENTS

Figure 1:
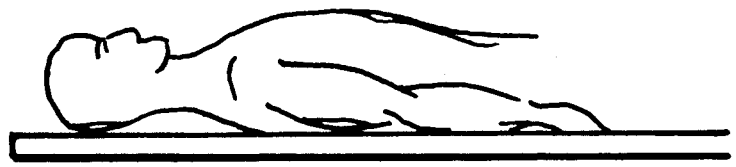
FIG. 1 shows in side view a patient in supine position.
Figure 2:
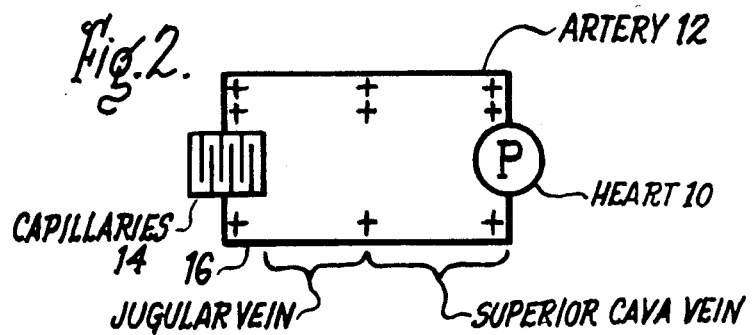
FIG. 2 shows a schematic hydraulic diagram of an upper portion of the vascular system of the supine patient of FIG. 1.
Figure 3:
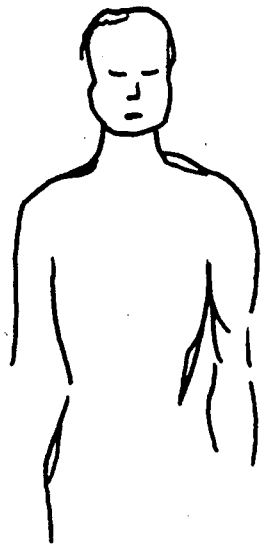
FIG. 3 shows in front view the patient in an upright position.
Figure 4:
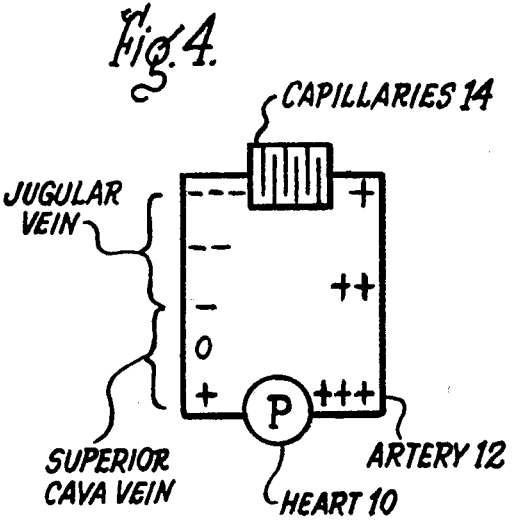
FIG. 4 shows a schematic hydraulic diagram of an upper portion of the cardio-vascular system of the upright patient of FIG. 3.

In the vast majority of surgical procedures, the patient is positioned in a supine position. Such a patient is illustrated in FIG. 1 and laterally registered therwith is the corresponding simplified cardiovascular diagram of FIG. 2 wherein, the pump/heart 10 pumps blood into artery 12, through a system of capillaries 14 in the head and neck and back through the vein 16. Vein 16 may, for example, represent a jugular vein plus the connecting superior cava vein. Note that the arterial pressure, indicated by "++", is greater than the venous pressure which lesser pressure is indicated by "+". The pressure in the artery 12 is essentially the same everywhere and the pressure in the vein 16 is also positive and about the same over the length of the vein. Substantially, all of the pump pressure is dropped across the capillaries 14.

However, when the patient is placed in upright position, the pressure in the lower portion of artery 12 increases because of the vertical hydrostatic pressure superimposed on the pump generated pressure.

It has been discovered that the pressures within the vein 16 are not analogous. It is theorized that this stems from the following blood flow behavior there.

Upon exiting the capillaries 14 into the uppermost vein portion, the blood is released into an environment of essentially no pressure or resistance and it tends to free fall under the pull of gravity. This induces a negative pressure that has heretofore led to air aspiration into a vein that is cut during surgery there. This negative pressure descreases as the blood descends and in the larger superior cava vein the "pressure" is essentially zero for a distance of several centimeters. A manometer pressure reading via a catheter port located in the upper portions of the superior cava vein cannot be made! As one adds fluid to the manometer the column always reads at the top end of the scale because the vein continues to take in the fluid. This positive reading is grossly inaccurate.

The falling blood forms a blood pool or reservoir that normally stands several centimeters high in the superior cava vein relative to the auricle of the heart. Positive pressures in this pool will, of course, reflect the depth in the pool at which the measuring catheter port is located. The positive pressure at the entrance to the auricle serves to prime the heat pump. This pre-load pressure, as may be measured by a catheter of this invention, provides important information to physicians regarding the possible excess loss of patient blood, pumping efficiency of the heart and other vital signs that are of crucial interest to the attending anesthesiologist.

The tip of the multichannel central venous pressure catheter 20 of this invention is illustrated in FIG. 5 and includes an elongated tube or sheath. The tube 22 encases three lumens 24, 26, 28, each providing a separate pneumatic or hydraulic channel through the tube 22. An inflatable balloon 30 surrounds a portion of the tube 22.

Lumen 24 provides a channel through tube 22 connecting to a distal port 32 in the tube 22 at the extreme tip end thereof. Lumen 26 provides a channel through tube 22 connecting to a proximal port 34 in tube 22. Lumen 28 provides a channel connecting to a pair of ports 35 and 36 in the tube leading to a chamber 38 formed between the normally deflated elastic balloon 30 and outer surface of the tube 22. Only one port 35 or 36 is essential, but two provide redundancy for added reliability, especially during deflation of the balloon 30.

When lumen 28 is pressurized, the deflated balloon 30 expands and inflates; the amount of pressure in lumen 28 determines the degree of expansion of balloon 30.

Referring to FIG. 5, the catheter 20 is designed to be inserted into the superior cava vein 38 by means of a wire introducer (not shown). For this purpose the distal most port 32 must be directly open to accommodate this wire. Since catheter 20 should be guided within venous vessels, the diameter preferably should not exceed 3 mm in diameter as to cause minimum blockage to blood flow there as well as to prevent serious wall damage due to its insertion. The diameter of the fully inflated balloon 30 is about 2.5 cm.

The fully inflated balloon 30 may have a plurality of ridges or scallops (not shown) that run in a parallel direction to the axis 40 of the balloon-surrounded tube 22. Such ridges cause a more even and less turbulent flow and direct blood flow in discrete ducts formed between the ridges around the balloon. A tendency for thrombus formation there may be reduced by use of such scalloped balloon.

Another essentially distal port 37 is within a centimeter away from distal port 32 and is located in the side wall of catheter tube 22. Port 37 is connected to the same lumen 24 as is distal port 32 This is to guard against the possibility that distal port 32 will be partially blocked (after the wire is withdrawn) by abutting perpendicularly on the vein wall which occurrence may give a false differential pressure indication.

Lumen 24 is connected to a manometer 46 and the lumen 26 is connected to another manometer 48 so that the pressures at the distal port 32/37 and the proximal port 34 may be measured.

Insertion of the catheter 20 is most safely accomplished when the patient is about supine with the head slightly down, because in this position the venous pressuure in the neck becomes a positive allowing the full distention of the vein, and because there is no threat of air aspiration.

The tip end of the catheter 20 is introduced into the left 42 or right 44 jugular vein or into the left or right subclavian vein 41. Catheter 20 is then pushed into the superior cava vein 38 with the balloon 30 deflated. With further gentle urging the tip of the catheter is pushed into the right angle auricle 43 of the heart 58 and further through the mitral valve 46. This even is immediately recognized by observing the greatly increased pressure excursions sensed via port 32 and lumen 24.

The catheter is thereupon withdrawn a distance of about 2½ centimeters so that the distal port 32 is located about in the middle of the positive pre-load pressure region that includes the lower 2 centimeters of the superior cava vein and the right auricle 43.

This is the preferred position because when the patient is subsequently placed in an upright position, the blood pressure in this lower region is a small positive pressure (e.g. about 4 cm H₂O) relative to that of the ambient atmosphere. It is a pre-load pressure that serves to prime the heart pump. But at higher points within the superior vein the pressure is very nearly zero, or equal to the atmospheric environment before the balloon is inflated.

Once insertion and positioning is accomplished, the central venous pressures at lumens 24 and 26 should be recorded. These pressures are normally in the range of 8 to 12 cm H₂O and should be equal to each other, e.g. ports 34 and 32 are zero.

The patient is then asked to sit up. New pressure readings should be recorded. The differential pressure will correspond to the pressure of the falling blood at the vertical distance between the distal port 32 and the proximal port 34 but the pressure at the proximal port 34 as measured by a manometer connected to lumen 24 will not be reliably indicated as has been explained above. The deflated balloon is gradually inflated by squeezing syringe 50 filled with a known volume of saline solution. The pressure at the proximal port 34 will increase and thereafter be subject to reliable measurement.

When the differential pressure between ports 32 and 34 equals the hydraulic pressure differential due to gravity plus the small pressure difference due to blood flow in the vein between the distal port 32 and the site of the head or neck at which surgery is to begin then the balloon is optimally expanded to create at the site of surgery a near zero pressure relative to the ambient air such that neither venous bleeding nor air embolism will occur.

This differential pressure can be closely predicted knowing the vertical distance between the distal port and the site of surgery. The volume of saline solution used is recorded which is a measure of the degree of balloon inflation. The balloon is deflated, the patient returned to horizontal position. Anesthesia begins. The patient is then positioned in the upright position (sat up) for proper surgical exposure. New pressure readings are made before surgery begins. The balloon 30 is again gradually increased until the differential pressure readings in manometers 46 and 48 indicate zero pressure at the middle of the surgical incision. e.g. by injecting the above-noted amount of saline solution into the balloon 30.

Changes in cardiac output, will cause a change in the differential pressures between ports 32 and 34 (when the balloon is inflated) and it is therefore necessary to continuously monitor the differential pressure and to make re-adjustments of the balloon size to maintain the above-noted optimum pressure differential. Adequate anesthesia levels can usually be administered to substantially stabilize the cardiac output. However, it is anticipated that automatic means can be employed, if necessary, to sense the differential ports pressure and make the indicated balloon size adjustments.

Thus, the construction of the catheter of this invention is such that the balloon may be positioned in the more predictable upper region of the superior cava vein for most reliably blocking and adjusting the blood pressure in veins at the site of surgery. At the same time, the distal port is located at from 5 to 12 centimeters below and submersed in the blood pool at the lower superior cava vein for continuous and reliable monitoring of pre-load blood pressures. Heretofore, it was not recognized that a catheter port in any portion of the superior cava vein of an upright patient would provide misleading information and the catheter and procedure of this invention overcame that problem of reliability as well as making more reliable the balloon control of venous pressures at a region of the head or neck.

What is claimed is:

1. A central venous pressure catheter for insertion in the cava vein of a patient to prevent air aspiration through cut veins of the head or neck during surgery on the patient in an upright position comprising:
    (a) an elongated flexible tube containing a plurality of lumens adapted for insertion into the superior cava vein of a patient via a jugular or subclavian vein;
    (b) one distal port in a side wall of said tube and within 1 centimeter of the tip end of said tube, said one distal port being connected to a first of said lumens;
    (c) a pneumatically or hydraulically inflatable balloon mounted about and on the outside of said tube at a distance of from 5 to 12 centimeters away from said one distal port; and
    (d) a proximal port in said catheter side wall located on the other side of said balloon from said distal port.

2. The catheter of claim 2 wherein said one distal and proximal ports are spaced no farther apart than 15 centimeters.

3. The catheter of claim 2 wherein said one distal and proximal ports are 10 centimeters apart.

4. A method for preventing air embolism in a patient in an upright position undergoing surgery of the head or neck comprising:
    (a) placing a patient in a supine position and pushing a tip of a central-venous-pressure multi-lumen catheter into a subclavian or a jugular vein of said patient, three ports in the wall of said catheter in communication, respectively, with three of said lumens, one of said ports being inside an inflated balloon formed about said catheter, a distal of said ports of said catheter tip being spaced away from said balloon by from 5 to 12 centimeters and a proximal of said ports being on the other side of said balloon from said distal port;
    (b) positioning said catheter so that said inflatable balloon portion of said catheter is located in an upper region of the superior cava vein of said patient and said tip and distal port are within the normally positive pre-load pressure region that includes the right atrium and the lower 2 centimeters of said superior cava vein;
    (c) placing said patient in the upright position;
    (d) measuring the differential pressure between said proximal and distal ports; and
    (e) inflating said balloon to partially obstruct the blood flow in said cava vein and raise said measured differential pressure to the blood-manometric pressure level corresponding to the vertical distance between said distal port and the site of said surgery so that the blood pressure at the site of surgery relative to the environment is near zero.

5. The method of claim 4 wherein said positioning includes first pushing said catheter tip via said right auricle through the heart mitral valve and just into the right ventricle as is indicated by a radical increase in heart-pumping-induced excursions of blood pressure measured via said distal port; and subsequently withdrawing said catheter within about one to three centimeters so that said balloon is located in said upper cava vein region.

6. The method of claim 4 wherein said distal and proximal ports are spaced no farther apart than 15 centimeters.

7. The method of claim 6 wherein said distal and proximal ports are 10 centimeters apart center to center.

8. The catheter of claim 1 additionally comprising another distal port positioned at the tip end of said tube and connected to said one lumen.

* * * * *